(12) United States Patent
Hirabayashi et al.

(10) Patent No.: US 6,989,531 B2
(45) Date of Patent: Jan. 24, 2006

(54) MASS SPECTROMETER

(75) Inventors: Atsumu Hirabayashi, Kodaira (JP);
Masako Ishimaru, Tokyo (JP);
Masahiro Yamaoka, Hachioji (JP)

(73) Assignee: Hitachi High-Technologies Corporation, Ltd., Tokyo (JP)

( * ) Notice: Subject to any disclaimer, the term of this patent is extended or adjusted under 35 U.S.C. 154(b) by 41 days.

(21) Appl. No.: 10/875,635

(22) Filed: Jun. 25, 2004

(65) Prior Publication Data

US 2005/0092917 A1    May 5, 2005

(30) Foreign Application Priority Data

Oct. 31, 2003    (JP)   .............................. 2003-371500

(51) Int. Cl.
*H01J 49/10*    (2006.01)

(52) U.S. Cl. ........................ 250/288; 250/282; 250/281
(58) Field of Classification Search ................ 250/288, 250/281, 282
See application file for complete search history.

(56) References Cited

U.S. PATENT DOCUMENTS

| | | | |
|---|---|---|---|
| RE34,757 E | * | 10/1994 | Smith et al. .................. 250/288 |
| 5,572,023 A | * | 11/1996 | Caprioli ....................... 250/288 |
| 5,898,175 A | * | 4/1999 | Hirabayashi et al. ........ 250/288 |
| 6,114,693 A | * | 9/2000 | Hirabayashi et al. ........ 250/288 |
| 6,384,411 B1 | * | 5/2002 | Hirabayashi et al. ........ 250/288 |
| 6,667,474 B1 | * | 12/2003 | Abramson et al. ........... 250/288 |
| 6,737,640 B2 | * | 5/2004 | Kato ............................ 250/281 |
| 6,753,521 B1 | * | 6/2004 | Park et al. .................... 250/282 |

OTHER PUBLICATIONS

Paul Kebarle et al., "From Ions in Solution to Ions in Gas Phase", Analytical Chemistry, vol. 65, No. 22 (Nov. 15, 1993), pp. 972-985.
Matthias S. Wilm et al., "Electrospray and Taylor-Cone Theory, Dole's Beam of Macromolecules at Last?", International Journal of Mass Spectrometry and Ion Processes, vol. 136 (1994), pp. 167-180.
Andrew J. Link et al., "Direct Analysis of Protein Complexes Using Mass Spectrometry", Nature Biotechnology, vol. 17 (Jul. 1999), pp. 676-682.
Tohru Natsume et al., "A Direct Nanoflow Liquid Chromatography-Tandem Mass Spectrometry System for Interaction Proteomics", Anal. Chem., vol. 74 (2002), pp. 4725-4733.

* cited by examiner

*Primary Examiner*—John R. Lee
*Assistant Examiner*—Johnnie L Smith, II
(74) *Attorney, Agent, or Firm*—Reed Smith LLP; Stanley P. Fisher, Esq.; Juan Carlos A. Marquez, Esq.

(57) ABSTRACT

The invention relates to an LC/MS interface provided with structure that the end of a spray capillary is rarely damaged and the object is to provide the LC/MS interface which a general user can easily operate, which inhibits the extension of a separation band and the deterioration of detection sensitivity and which enables high separation and sensitive analysis. A metallic member having a hole for connecting a separation column and a spray capillary and a resin member for fixing the upstream side of the short spray capillary are used. Further, to enhance operability, spray ionization using gas spraying is used.

20 Claims, 9 Drawing Sheets

MASS SPECTROMETER

CLAIM OF PRIORITY

The present invention claims priority from Japanese application JP 2003-371500 field on Oct. 31, 2003, the content of which is hereby incorporated by reference on to this application.

BACKGROUND OF THE INVENTION

The present invention relates to a liquid chromatograph/mass spectrometer(LC/MS) that separates and analyzes liquid mixture, particularly relates to a protein analysis (proteomics) system and a glycan analysis (glycomics) system that on-line analyze organism-related substance mixed liquid to which pretreatment such as enzyme digestion is applied. In a field of the organism-related substance analysis, it is regarded as important to separate and analyze a sample of an extremely minute amount.

LC/MS has been used for analyzing an organismal sample of a minute amount. However, as an amount of a sample is reduced, high separation (high concentration) in LC (the liquid chromatograph) and the enhancement of the efficiency of ionization in an LC/MS interface have been recognized as important. Spray ionization such as electrospray is applied to the ionization technique of the interface and it is known that the less a liquid flow rate is, the more the efficiency of ionization tends to be enhanced. Electrospray ionization is described in Analytical Chemistry, Vol. 65, 1993, pp. 972A to 986A for example. In the interface using electrospray ionization, high voltage of approximately a few kV is applied between liquid taken in a spray capillary and an ion intake port (a metallic sampling orifice) of a mass spectrometer. Charged fine droplets leap out of liquid at the end of the spray capillary toward the ion intake port of the mass spectrometer and gaseous ions are generated based upon the charged fine droplets by the effect of evaporation.

In the meantime, the reduction of a liquid flow rate in LC and high separation can be compatible. Therefore, a new interface based upon nanoLC in which LC separation occurs at a little flow rate at which a liquid flow rate is at a level of a nanoliter and spray ionization using a nanospray having small-sized configuration in which efficient ion generation is enabled at a little flow rate has been used. The nanospray is described in International Journal of Mass Spectrometry and Ion Processes, Vol. 136, 1994, pp. 167 to 180 for example. In an interface using the nanospray, a spray capillary the end of which is tapered is used. The nanospray is acquired by making a spray capillary of an electrospray fine and it is considered that an ion generation principle is the same. However, when the surface area of liquid exposed to the end of the spray capillary is large, a liquid flow rate and an amount of evaporation at the end of the spray capillary becomes equal and ionization becomes unstable or is stopped. This problem becomes remarkable as a liquid flow rate decreases and the size of the end of the spray capillary is required to be miniaturized corresponding to the reduction of a flow rate. Therefore, the size at the end of the spray capillary of the nanospray is often required to be in units of a micron and the spray capillary is often made of fused silica and glass. For a metallic spray capillary, as there is a problem in working, the size of the end is currently larger than 30 $\mu$m. Therefore, at an extremely little flow rate of 200 nanoliter/minute or less, a spray capillary made of fused silica and glass is often used.

In U.S. Pat. No. 5,572,023, description related to a column-integrated LC/MS interface in which an LC separation column is plugged into a spray capillary the end of which is tapered is found. In this configuration, the end of the separation column and the end of the spray capillary are substantially coincident. Therefore, an effluent separated in the LC column is sprayed without being substantially influenced by diffusion. As a result, a highly separated (concentrated) sample is efficiently ionized and can be analyzed in a mass spectrometer. Besides, in Nature Biotechnology, Vol. 17, 1999, pp. 676 to 682, an example that a reverse-phase column is first plugged into a spray capillary made of fused silica and next, an ion exchange column is plugged is described. In this example, two-dimensional LC separation can be realized by a simple system by changing the composition of mobile-phase liquid. For ionization, electrospray ionization which is one type of spray ionization is often used.

In the electrospray ionization, high voltage is required to be applied between liquid at the end of the spray capillary and an ion intake port of a mass spectrometer. Therefore, the spray capillary is fixed to a metallic union (see FIG. 2) and an electrode is often installed on the metallic union. As acid such as formic acid is added to the mobile-phase liquid, the metallic union and the liquid at the end of the spray capillary electrically conduct. The mobile-phase liquid is taken in the metallic union at a fixed flow rate from a capillary on the upstream side by a pump system and is taken in the spray capillary.

The spray capillary integrated with the separation column described above is often required to be replaced. 1) The reason is that nonvolatile materials deposit by the evaporation of the liquid at the end and may clog the spray capillary. 2) The reason is that the separation column is clogged with the materials of the sample. 3) The reason is that the separation column is contaminated. The spray capillary itself is often made of fused silica and glass, the end of the spray capillary has size in units of a micron and is very easily damaged. Actually, the end of the capillary is damaged only by being touched to a someone in replacing spray capillaries. The damaged capillary cannot be used. Therefore, close attention is required in replacing spray capillaries.

Figure 2:
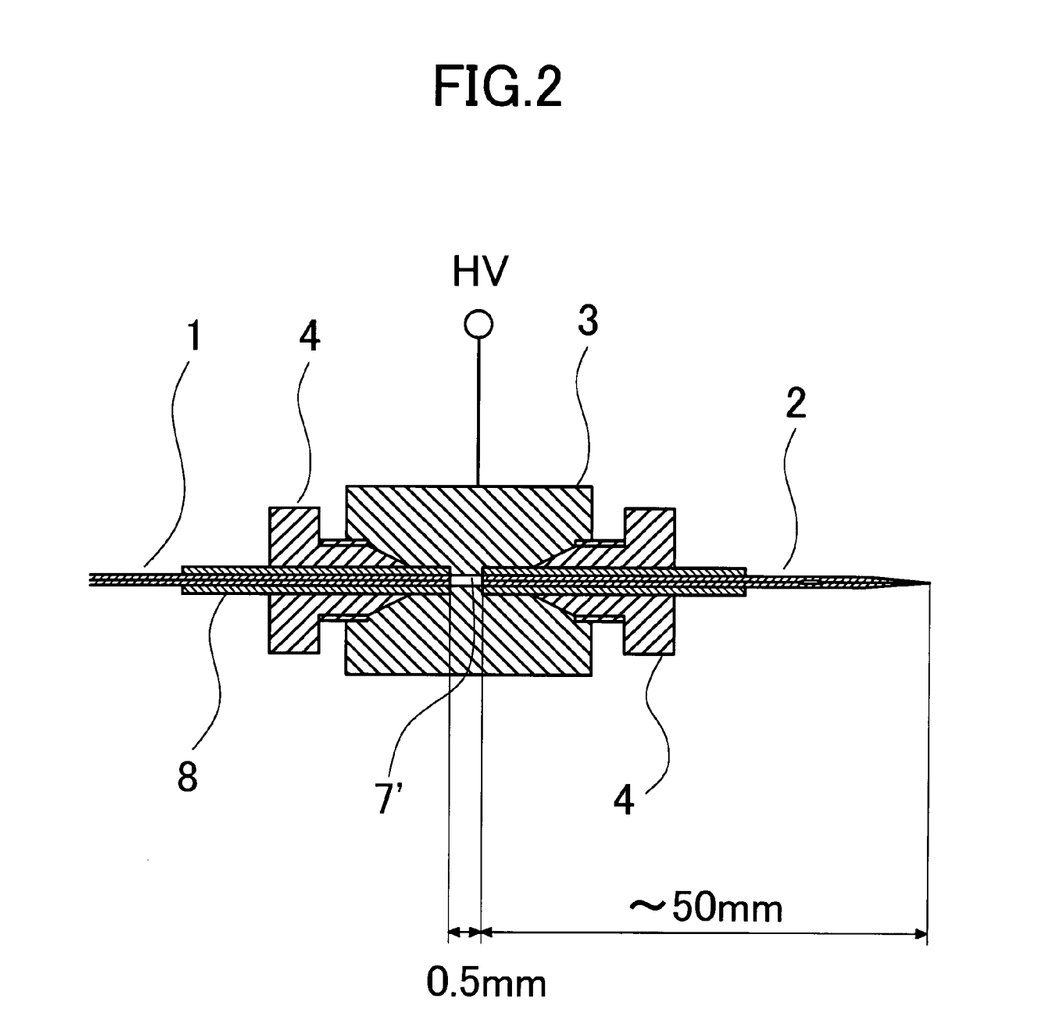
FIG. 2 is a sectional view showing an ion source in an interface in which a spray capillary and a separation column are separated and are connected by a metallic union.

Then, as shown in FIG. 2, a trial that a spray capillary 2 and a separation column 1 are separately formed and are connected via a metallic union 3 is made. For example, in Analytical Chemistry Vol. 74, 2002, pp. 4725 to 4733, an example using this configuration is given. In this configuration, high voltage is applied between the metallic union 3 and an ion intake port (not shown) of a mass spectrometer so as to generate ions.

SUMMARY OF THE INVENTION

As described above, there is a problem that in case a spray capillary the end of which is tapered is replaced, close attention is required to prevent the end of the spray capillary from being damaged. Particularly in the case of an interface in which a separation column is integrated, this problem is serious because an economic burden is increased.

Besides, in case the separation column 1 and the spray capillary 2 are connected via the metallic union 3 as shown in FIG. 2, the spray capillary 2 can be fixed to the union 3. However, his configuration has a problem that the occurrence of dead volume cannot be neglected. Further, in electrospray ionization, high voltage is applied between liquid at the end of the spray capillary and an ion intake port of a mass spectrometer. As the end of the spray capillary and the ion intake port of the mass spectrometer are subtly contaminated, the position of the end of the spray capillary and applied voltage are adjusted when spraying is started and the sensitivity of the instrument is required to be optimized. There is a problem that a high skill is required for such fine control and such structure is difficult for a general user to handle.

It is considered that as the structure shown in FIG. 2 has the above-mentioned problems, it is difficult to be widely popularized among general users though nanoLC/MS is regarded as important.

As it takes a few seconds to a few minutes until separated liquid effluent from the separation column 1 is sprayed in the configuration shown in FIG. 2, the liquid separated in the separation column is forced to be influenced by diffusion. Besides, dead volume in the union 3 and the spray capillary 2 becomes appreciable and separated samples outgoing from the separation column 1 are influenced by diffusion. These are connected directly with a problem of the extension of a separation band and the deterioration of detection sensitivity. Besides, as the spray capillary 2 is fixed to the metallic union 3 by a fixture 4 such as fittings and a nut to fix the spray capillary 2, it is difficult to shorten the spray capillary 2 and the spray capillary is required to normally have the length of approximately 50 mm or more. Further, a hole is made in the center of the metallic union 3, however, the length of the hole is required to be approximately 0.5 mm or more because of a problem of a working process. In case the spray capillary 2 is long and in case the length of the hole in the center of the metallic union 3 is too long, a problem that dead volume becomes appreciable.

A first object of the invention in view of the above-mentioned problems is to provide an LC/MS interface having structure that the end of a spray capillary is hardly damaged. Besides, a second object of the invention is to provide an LC/MS interface in which the extension of a separation band and the deterioration of detection sensitivity are inhibited and high separation and high-sensitivity analysis are enabled. Further, a third object of the invention is to provide an LC/MS interface which is easy for a general user to use and which has high operability.

To achieve the objects, a resin member that supports the spray capillary and a metallic member which supports a separation column (or a hollow capillary) and in which a hole for connecting the separation column (or the hollow capillary) and the spray capillary is made are used. Besides, the spray capillary is formed shortly and the upstream side in a direction of a main flow of a sample is fixed by the resin member. Besides, spray ionization using gaseous spray may be also used to enhance operability.

A mass spectrometer according to the invention is provided with a pump for conveying a sample, a tube for conveying the sample, a spray tube for taking the sample conveyed from the tube, a metallic member that supports a tube, a resin member that supports the spray tube, a mass spectrograph that analyzes the mass of an ion sprayed from the spray tube and an information processing unit that processes the result of analysis by the mass spectrograph for example, and is characterized in that the resin member is closely in contact with the peripheral surface of the spray tube except an open face at a sample intake end, at least a part of the resin member is in contact with the metallic member and a sample outlet of the tube is located in the vicinity of the sample intake end of the spray tube.

A mass spectrometer according to the invention having another configuration is provided with a pump for conveying a sample, a tube for conveying the sample, a spray tube for taking the sample conveyed from the tube, a metallic member that supports the tube, a housing for housing the metallic member, a resin member that supports the spray tube, a mass spectrograph that analyzes the mass of an ion sprayed from the spray tube and an information processing unit that processes the result of analysis by the mass spectrograph, and is characterized in that a sample outlet of the tube is located in the vicinity of a sample intake end of the spray tube and the housing and the resin member are fitted.

A mass spectrometer according to the invention having another configuration is provided with a pump for conveying a sample, a tube for conveying the sample, a spray tube for taking the sample conveyed from the tube, a first supporting member that supports the tube, a second supporting member that supports the spray tube, a mass spectrograph that analyzes the mass of an ion sprayed from the spray tube and an information processing unit that processes the result of analysis by the mass spectrograph, and is characterized in that the second supporting member is formed by material lower in hardness than the first supporting part and a sample outlet of the tube is located in the vicinity of a sample intake end of the spray tube.

For members for mass spectrometry according to the invention, for example, there are the tube for conveying a sample, the spray tube for taking the sample conveyed from the tube, the metallic member that supports the tube, the resin member that supports the spray tube and a cover that includes a part protruded outside the resin member of the spray tube, and the members are characterized in that the resin member is closely in contact with the peripheral surface of the spray tube except the open face at the sample intake end, at least a part of the resin member is in contact with the metallic member and the sample outlet of the tube is located in the vicinity of the sample intake end of the spray tube.

Dead volume around the separation column (or the hollow capillary) and the spray capillary can be reduced possibly by adopting the above-mentioned configuration. Besides, detection sensitivity can be enhanced, sharpening a separation band by reducing the dead volume.

DETAILED DESCRIPTION OF THE PREFERRED EMBODIMENTS

Figure 1:
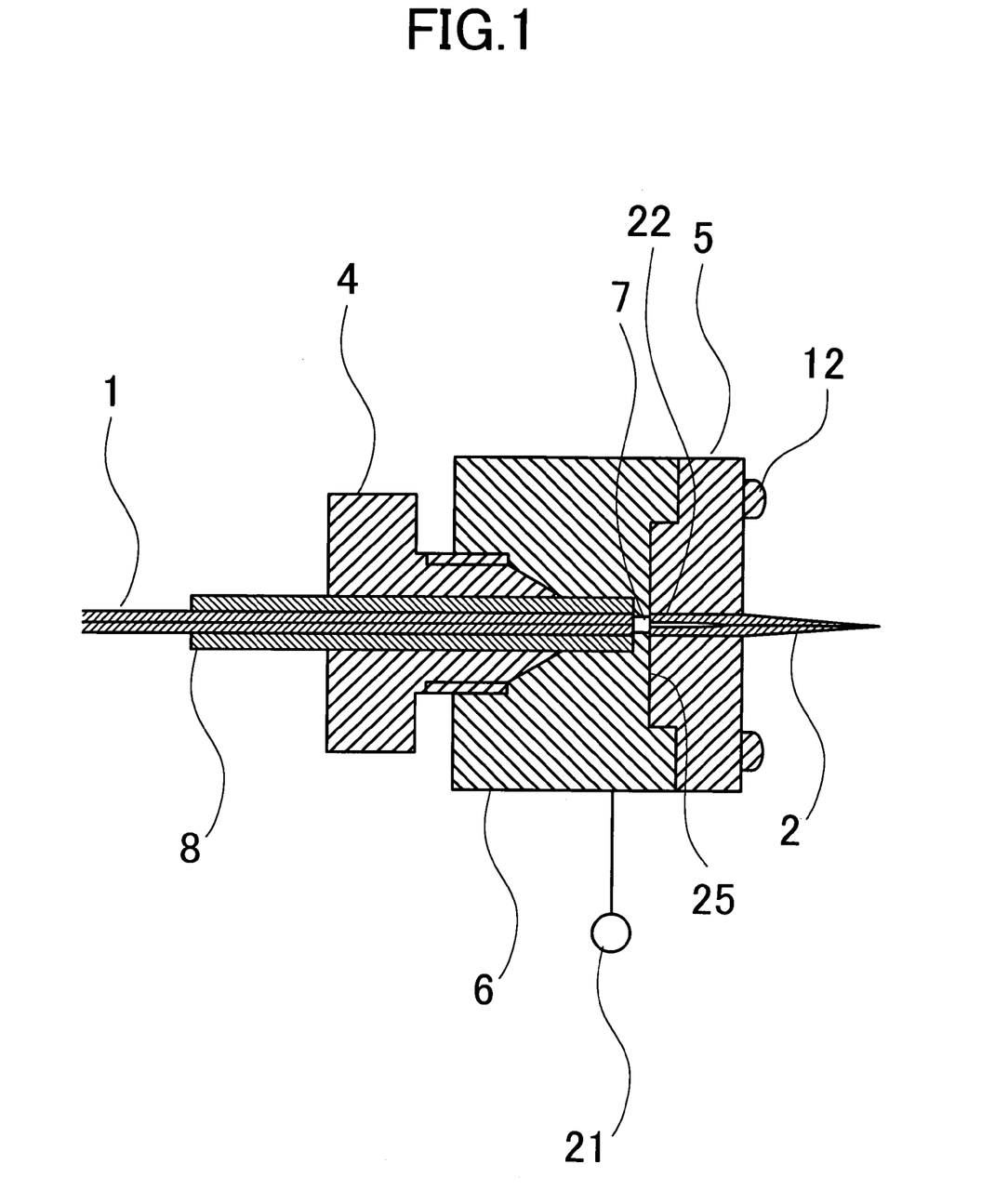
FIG. 1 is a sectional view showing an ion source in an interface in one embodiment of the invention.

FIG. 1 is a sectional view showing an ion source in an interface in one embodiment of the invention. The upstream side in a direction of a main flow of a sample of a spray capillary 2, that is, a sample intake end is fixed by inserting it into a resin member 5. As shown in FIG. 1, the peripheral surface of the spray capillary 2 except the open surface at the sample intake end is closely in contact with the resin member 5 inside the resin member 5. The end (approximately 7 mm) of the spray capillary 2 is often tapered and the outside diameter is fixed to the resin member 5 in a fixed part (approximately 3 mm or more). As described above, the spray capillary 2 is fixed only by inserting it into the resin member 5. It is desirable that the whole length of the spray capillary 2 has a value in a range from approximately 1 mm to approximately 50 mm, considering that the thickness in the direction of the main flow of the sample of the resin member 5 is approximately 1 mm or more and that the shorter the length of the spray capillary is, the more desirable it is so as to reduce dead volume. Besides, the length of a protruded part outside from the resin member 5 of the spray capillary 2 has a value in a range from approximately 0.1 mm to approximately 50 mm, considering that the spray capillary 2 is fixed up to the vicinity of the end on the downstream side in the direction of the main flow of the sample by the resin member 5 and that the thickness in the direction of the main flow of the sample of the resin member 5 is approximately 1 mm or more.

To enhance the precision of fixation, it is desirable that resin having flexibility and made of chemically stable material is used for the resin member 5. Concretely, it is desirable that Teflon (a trademark) (polytetrafluoroethylene), polyether ether ketone (PEEK) and material having the similar property to these are used. The resin member has a characteristic that it is made of material having lower hardness than at least a metallic member described later. The thickness in the direction of the main flow of the sample of the resin member may be arbitrary if the thickness is approximately 1 mm or more, however, considering the strength, it is desirable that the thickness is in a range from approximately 2 mm to approximately 8 mm.

In the meantime, the downstream side in the direction of the main flow of the sample of a separation column 1, that is, a sample outlet is fixed to the metallic member 6 by a fixture 4 such as fittings. The separation column is sometime made of a fused silica capillary the outside diameter of which is approximately 360 $\mu$m and in case the diameter is small as in such a case, it is sometimes difficult to directly fix the separation column by the fixture 4 such as fittings. In that case, it is convenient that after at least a part of the separation column is housed in a resin sleeve 8 made of PEEK and others, the separation column is fixed by the fixture 4. The resin member 5 is fixed to the metallic member 6 by a fixture such as a screw 12.

It is important to avoid the occurrence of dead volume and the leakage of the sample at a joint (in a fitted part 25) of the resin member supporting the spray capillary and the metallic member supporting the separation column. Therefore, it is necessary to possibly make a sample passage in each, that is, each cross section of the spray capillary and the separation column coincident and to substantially align each sample passage on a straight line of the separation column 1. When parts in which both members are touched are worked so that the parts are symmetrical based upon each central axis of both members in the direction of the main flow of the sample, each central axis of both members can be substantially made coincident in fixing. In case each sample passage is substantially positioned on the central axis of each member, the joining of the sample passages can be enhanced and the leakage of the sample at the joint can be prevented. Therefore, the resin member 5 and the metallic member 6 are required to be precisely worked so that they can be fitted.

A hole (An opening) 7 approximately 0.18 mm in diameter is made in the metallic member 6, an effluent outgoing from the separation column 1 passes the hole 7, and is led to the spray capillary 2 fixed to the resin member 5. The inside diameter of the hole (opening) 7 may be also smaller than the outside diameter of the sample outlet of the separation column and in that case, the leakage of the sample between the separation column and the hole can be effectively prevented. In a conventional type union shown in FIG. 2, the length of a hole 7' corresponding to the hole 7 is approximately 0.5 mm. However, according to this configuration, as structure that the resin member 5 and the metallic member 6 are fitted is easily worked, the length in the direction of the main flow of the sample of the hole 7 can be made approximately 0.1 mm. Considering that the lower limit of metal working is approximately 0.01 mm, the length can be set in a range from approximately 0.01 mm to approximately 0.5 mm. Gaseous ions are generated from the end (the inside diameter: approximately 8 $\mu$m) of the spray capillary 2 by applying high voltage of approximately 1.2 kV between an ion intake port of a mass spectrometer and the metallic member 6 (by applying high voltage in a position 21 shown in FIG. 1 connected to the metallic member 6) (electrospray ionization). Organismal ions are taken in a vacuum part from the ion intake port of the mass spectrometer. In such configuration, the length of the spray capillary 2 can be reduced up to approximately 10 mm (the sum of the length of the end and the length of a part fixed by the resin member, that is, 7 mm+3 mm). Further, the spray capillary 2 approximately 3 mm long can be also used by tapering a hole into which the spray capillary is inserted of the resin member 5 so as to fix the tapered part of the end of the spray capillary by the resin member. The hole 7 of the metallic member 6 and the total dead volume of the spray capillary 2 can be reduced by several times by shortening the hole 7 and/or the spray capillary 2, compared with those in the example shown in FIG. 2. This means that the dilution of an effluent outgoing from the separation column is inhibited and analysis at high sensitivity is enabled.

Figure 9:
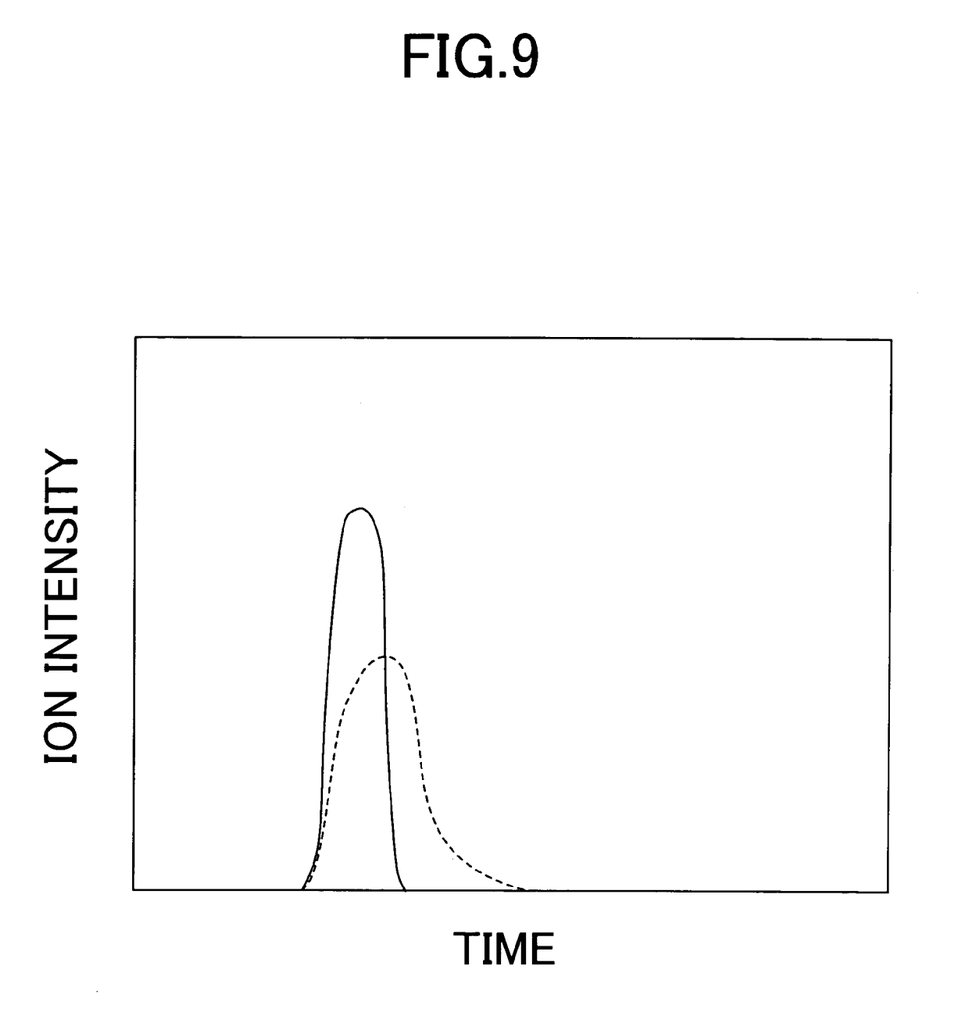
FIG. 9 shows a mass spectrometry chromatogram in one embodiment of the invention.

For example, in a mass spectrometry chromatogram acquired with this configuration, a separation band shown by a full line in FIG. 9 is acquired, however, in a chromatogram acquired with configuration shown in FIG. 2 in which dead volume is appreciable, even if the same ion is detected, a separation band shown by a dotted line is acquired. Concerning the separation band shown by the dotted line, not only ion intensity (peak intensity) is low but the bandwidth is extended and tailing also occurs. When dead volume is large, the cross section of a flow of fluid is substantially enlarged and the separation bandwidth is extended. As a result, the sample in a concentrated band is diluted. Infusion analysis in which sample solution of fixed concentration is taken in an ion source at a fixed flow rate and is analyzed can be easily performed by using a hollow fused silica capillary in place of the column 1. In this case, the downstream side in the direction of the main flow of the sample of the hollow fused silica capillary, that is, the sample outlet is fixed by the metallic member 6 because the downstream side is inserted into the metallic member.

Figure 3:
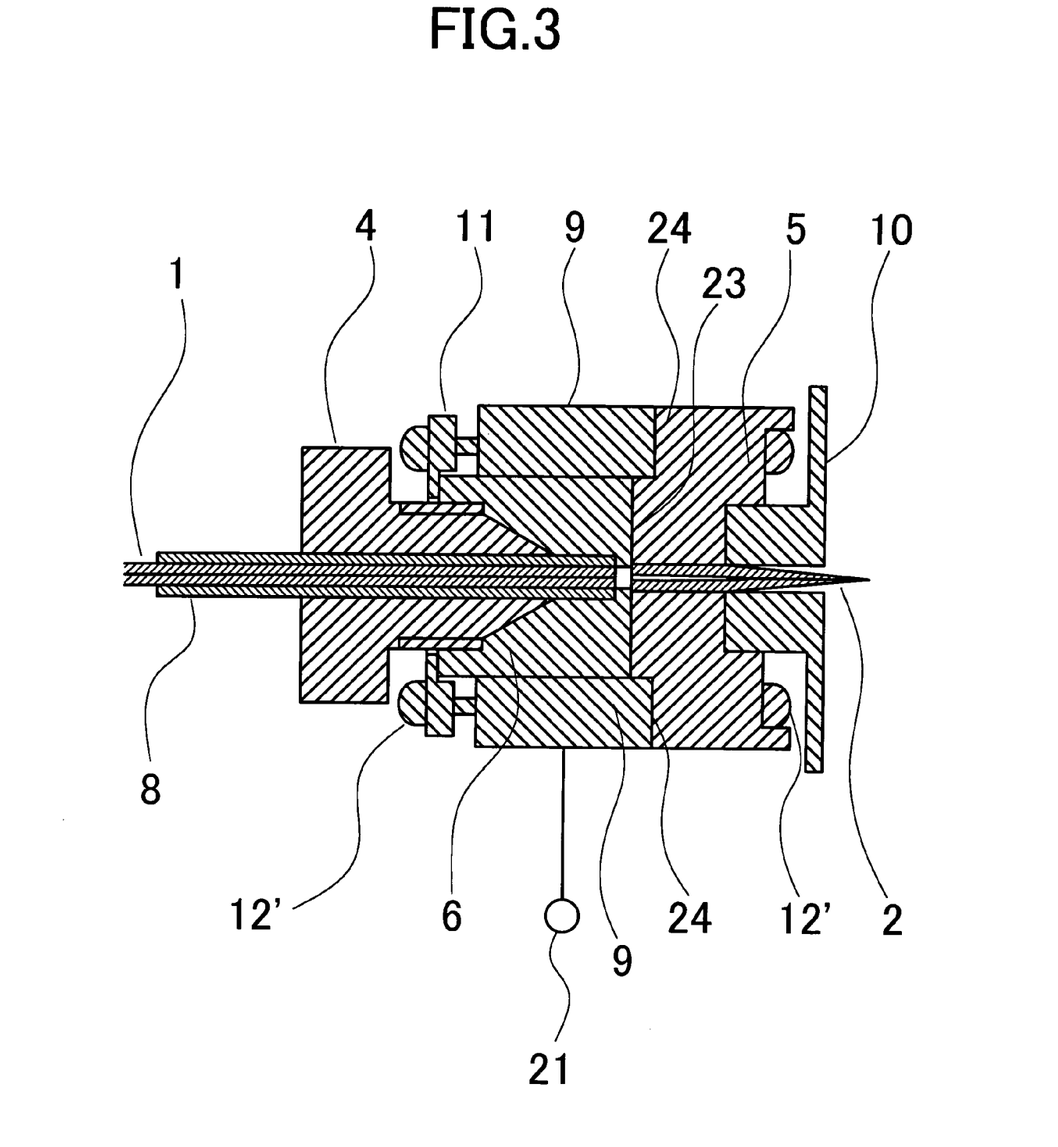
FIG. 3 is a sectional view showing an ion source in an interface in another embodiment of the invention.

Further, FIG. 3 is a sectional view showing an oil source in an interface in another embodiment of the invention. The basic structure of a resin member 5 that supports a spray capillary 2 and a metallic member 6 that supports a separation column 1 is the same as that in the embodiment shown in FIG. 1, however, a housing 9, a keep plate 11 and rear screws 12' are further used. The metallic member 6 having a hole 7 is fitted into the housing 9 and is pressed on the side of the resin member 5 by the keep plate 11 and the rear screws 12' from the rear. The resin member 5 is fixed to the metallic member 6 or the housing 9 by screws 12 and is pressed on the side of the metallic member 6 and the housing 9. As the resin member 5 is softer, compared with the metallic member 6, the resin 5 and the metallic member 6 are made closely in contact by pressing both and liquid can be prevented from leaking. The housing and the metallic member may be also formed so that they correspond to each irregularity, that is, the form of a fitted part of the resin member 5 as shown in FIG. 3. In FIG. 3, a concave portion 23 of the fitted part of the resin member 5 is in contact with at least a part of the metallic member 6. In the meantime, a convex portion 24 of the fitted part of the resin member 5 is in contact with at least a part of the housing 9. In this case, high adhesiveness is kept even if the resin member is deformed by pressure and a sample can be prevented from leaking. In this embodiment, for ionization, electrospray ionization is also used. In case the housing 9 touched to the metallic member 6 is made of metal, an electrode for the application of voltage required for electrospraying can be installed on the housing 9. Further, in case the resin member 5 is a dielectric, it is charged by the adhesion of ions and others and it may have an effect upon the generation of ions. It is desirable that charge is prevented in the resin member 5 around the capillary 2 and others by using a metallic cover 10 so that at least a part of the metallic cover is in contact with the resin member 5 and the metallic cover is located in the vicinity of a sample outlet of the spray capillary. The metallic cover 10 can be also utilized in the other embodiments. In this embodiment, as the sample can be prevented from leaking by enhancing the adhesiveness of the metallic member and the resin member, the similar or higher ion intensity to/than that in FIG. 9 can be acquired in a mass spectrometry chromatograph.

Figure 5:
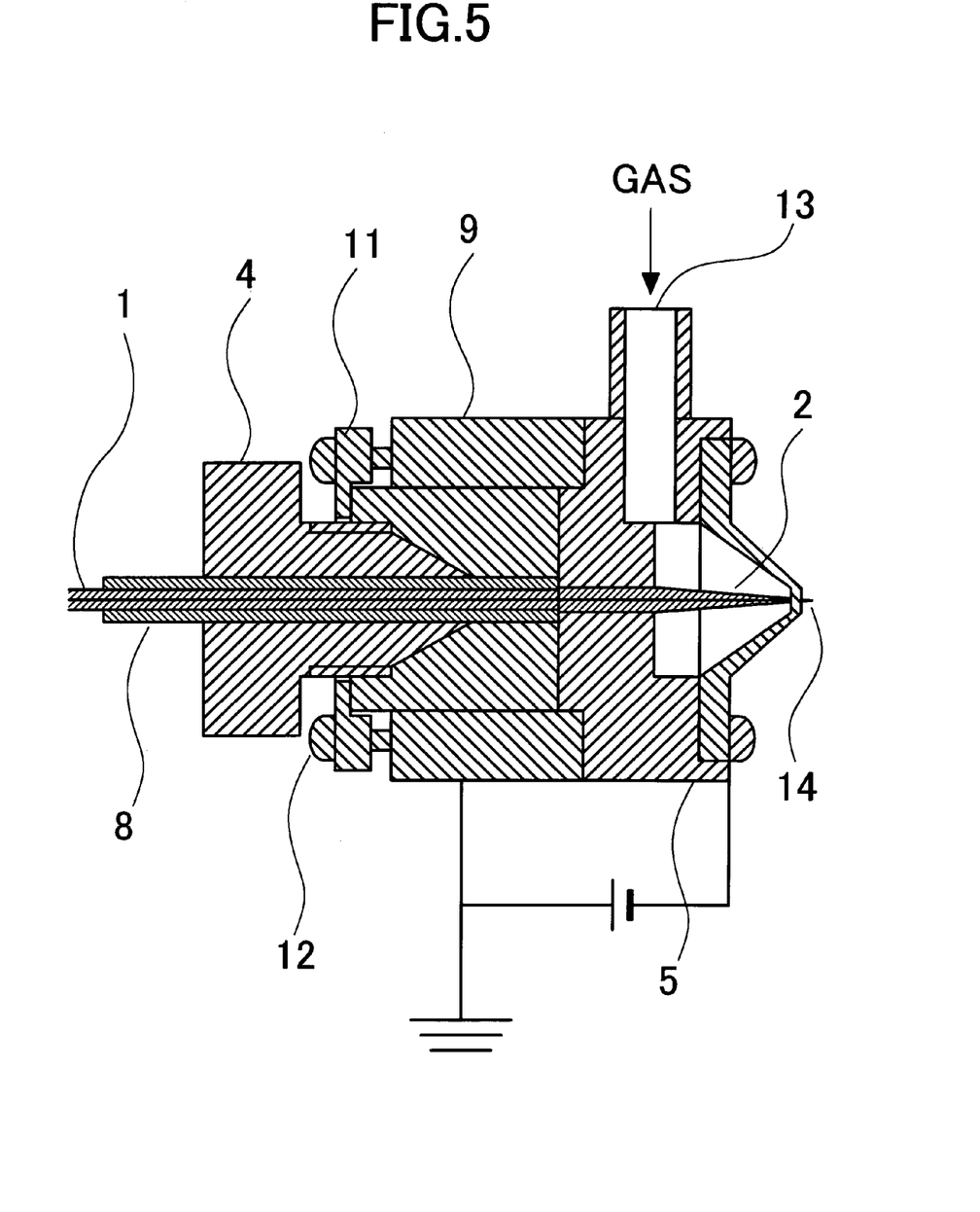
FIG. 5 is a sectional view showing an ion source in an interface that adopts ionization using gaseous spray together.

In the embodiment shown in FIG. 3, electrospray ionization is adopted for ionization. However, when ionization also using gas spraying is adopted, operability is greatly enhanced. FIG. 5 is a sectional view showing an ion source in an interface adopting ionization also using gas spraying. The basic structure is similar to the ion source shown in FIG. 3, however, inert gas such as gaseous nitrogen is taken from a gas intake port 13 and is exhausted outside from a metallic orifice 14. The end of a spray chip 2 is inserted into the metallic orifice 14 and gas flows outside along the end of the spray chip 2. It is desirable that the metallic orifice 14 is coaxial with the spray chip and is fitted to the resin member 5. A metallic electrode is installed on the metallic housing 9 touched to the metallic member 6 and a positive ion can be generated by turning the metallic housing 9 to ground potential and applying voltage of approximately −0.8 kV to the metallic orifice 14. In the ion source adopting such ionization, even if the flow rate of liquid is set to 20 nanoL/minute, the spray chip 2 having an end the inside diameter of which is approximately 15 μm can be used. This means that the end of the spray capillary 2 can be large-sized, compared with a case of ionization not using gas spraying together. As a result, the clogging by the deposition of nonvolatile materials of the end of the spray capillary 2 is inhibited and in addition, the strength of the end of the spray capillary 2 is also enhanced. In the ion source having such structure, ion generation efficiency is enhanced by approximately a few times, compared with a case that gas spraying is not used together. Further, subtle contamination at the end of the spray capillary and at an ion intake port of a mass spectrometer hardly has an effect, the position of the end of the spray capillary and applied voltage are not required to be adjusted when spray is started, and the sensitivity of the instrument is not required to be optimized. Therefore, the interface using such an ion source is suitable for an automated system and has a characteristic that the interface is easy for a general user to handle. In case electrospray ionization using gas spraying together is applied, the metallic housing 9 and the metallic orifice 14 are turned to the same potential, and voltage is applied between them and the ion intake port 15 of the mass spectrometer. As the size of the end of the spray capillary 2 is minute, voltage applied to the ion intake port of the mass spectrometer, the metallic housing 9 and the metallic orifice 14 is reduced, and ions can be generated by applying voltage of approximately 1.2 kV.

Figure 8:
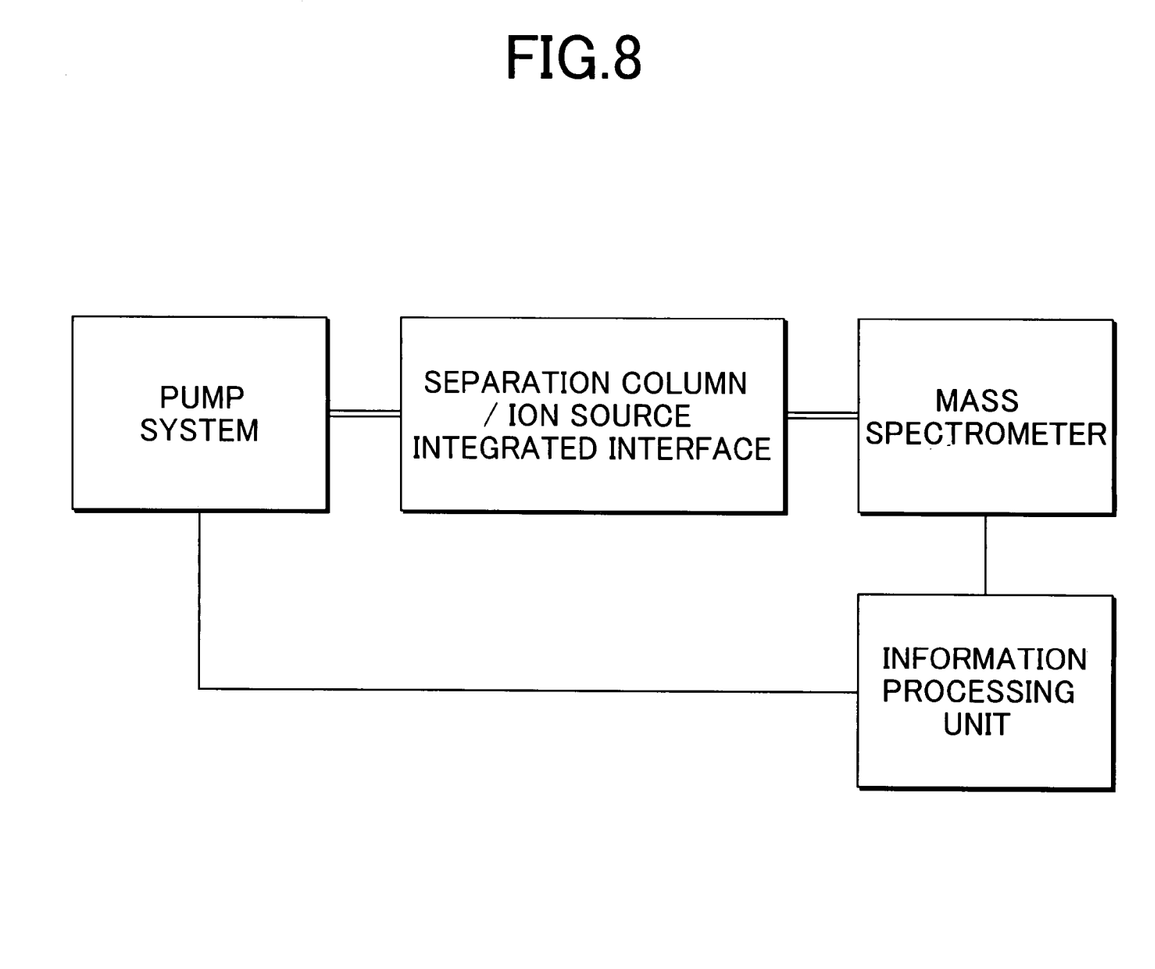
FIG. 8 is a block diagram showing a typical liquid chromatograph/mass spectrometer (LC/MS) in one embodiment of the invention.

FIG. 8 is a block diagram showing a typical liquid chromatograph/mass spectrometer (LC/MS) in one embodiment of the invention. A sample taken from an automatic sampler (or an injector) is sucked in the separation column. The mobile-phase sample is taken in the separation column at a fixed flow rate by a pump system, however, the separation column has a gradient, and the composition of the mobile phase temporally varies. When the composition of the mobile phase reaches a specific value, the substance sucked in the separation column is liberated to a mobile phase because an equilibrium condition rapidly changes and is taken in the end of the spray capillary 2 in a band (in a concentrated state). The sample converted to gaseous ions from the end of the spray capillary 2 is analyzed in the mass spectrometer and the output is analyzed in an information processing unit. In the invention, the separation column is integrated with the ion source in the interface. Besides, the information processing unit can exchange information with the pump system, the separation column/ion source integrated interface and the mass spectrometer.

Figure 4:
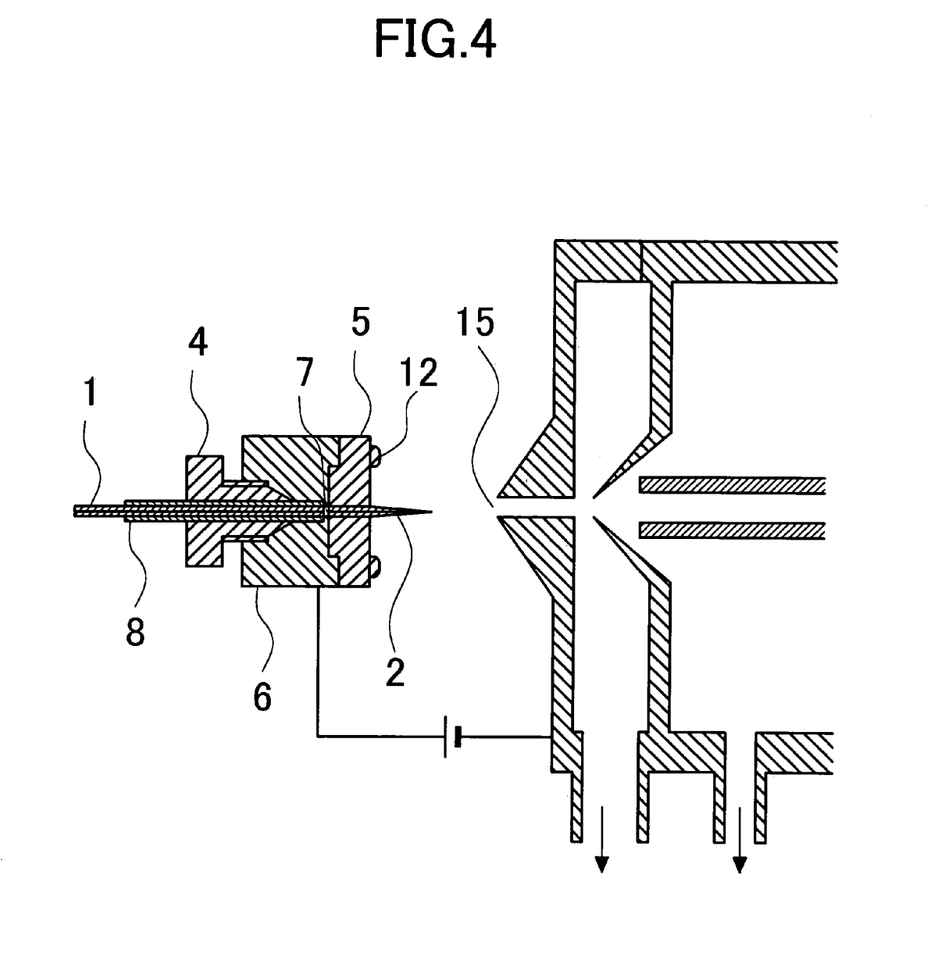
FIG. 4 is a sectional view showing the ion source and an ion intake port in the interface in one embodiment of the invention.

FIG. 4 is a sectional view showing the interface in one embodiment of the invention. In electrospray ionization, in case the highest ion detection sensitivity is required, the fine control for the ion intake port 15 of the position of the end of the spray capillary 2 and applied voltage is required. In case the column is replaced, the separation column 1 has only to be replaced and possibility that the end of the spray capillary 2 is damaged is very low.

Figure 6:
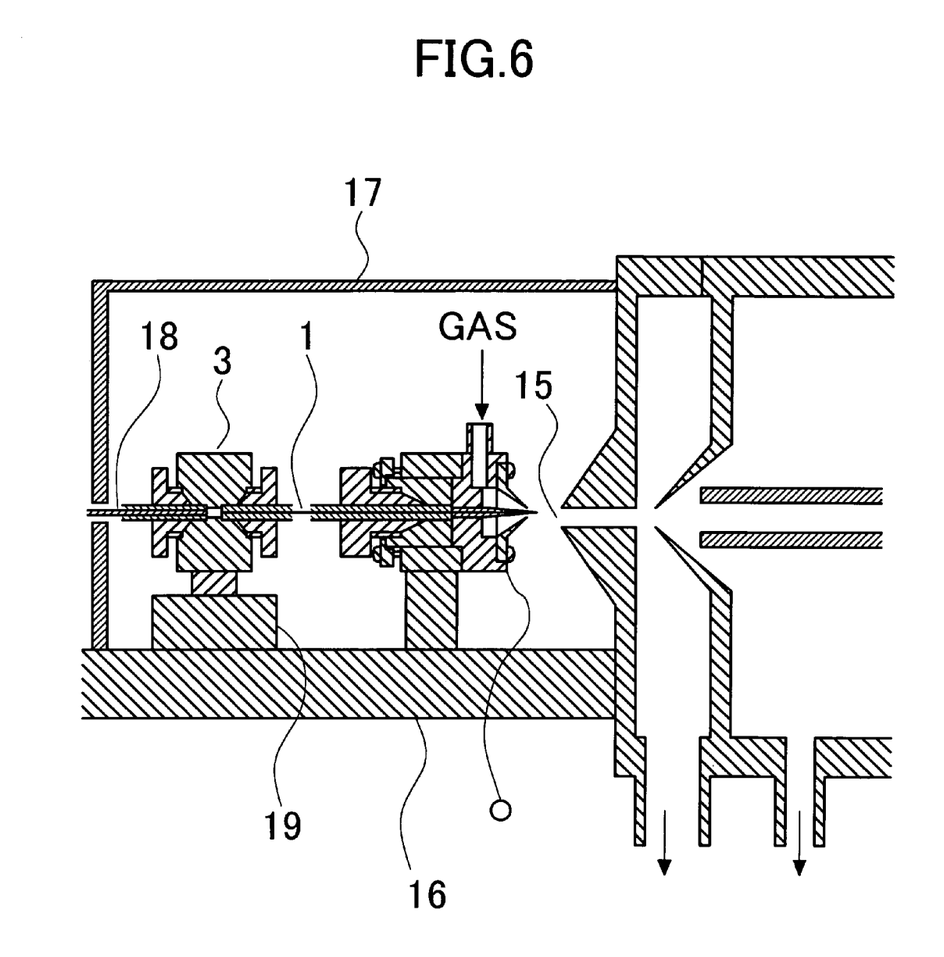
FIG. 6 is a sectional view showing the ion source in the interface in one embodiment of the invention.

FIG. 6 is a sectional view showing the interface in one embodiment of the invention. In ionization using gas spraying, the fine control for the ion intake port 15 of the mass spectrometer of a position of the ion source is not required as a rule and the ion source can be fixed to a table 16 fixed to the mass spectrometer. Concerning typical setting, the central axis of the spray capillary 2 is aligned with the center line of the ion intake port 15 and an interval of approximately 2 cm is made between them. The enhancement of operability by this can remarkably reduce a load onto a user. In case the column is replaced, the separation column 1 also has only to be replaced and possibility that the end of the spray capillary 2 is damaged is very low. Besides, the upstream side in the direction of the main flow of the sample of the separation column 1 is connected to a hollow capillary 18 connected to the pump system and a union 3. The hollow capillary is provided with a function for conveying liquid from a pump to the column. Particularly, in case the length of the separation column 1 is approximately 50 mm and is short, it is convenient that a support 19 for supporting the union 3 on the table 16 is provided. As the separation column 1 may be also fixed to the ion source after the separation column is fixed to the union 3, the support 19 can be easily moved on the table 16. In infusion analysis, a hollow capillary is adopted in place of the separation column 1 and sample liquid may be also taken by a syringe pump and others. It is desirable that a cover 17 is provided to the interface to avoid the effect of wind from the outside and the effect of the mixture of dust and outside air is interrupted.

Figure 7:
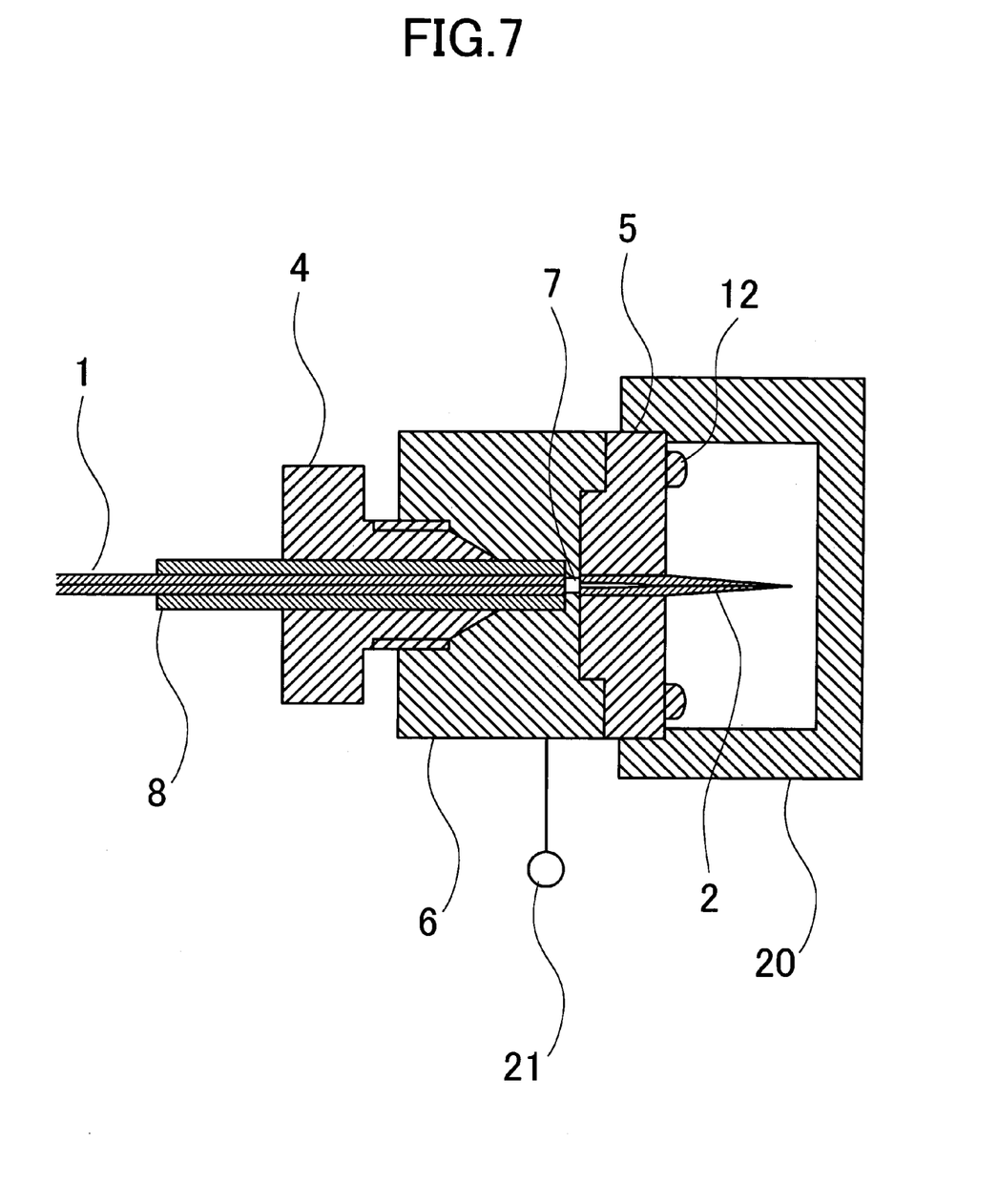
FIG. 7 is a sectional view showing the interface using a holder in one embodiment of the invention.

Attention is required to be paid to the movement of the ion source because the spray capillary 2 is slightly protruded from the end of the ion source. Then, when a protective enclosure 20 is prepared and is attached to the end of the ion source as shown in FIG. 7, fear that the end of the capillary 2 is damaged when the ion source is moved is removed and it is convenient.

According to the invention, the LC/MS interface having the structure that the end of the spray capillary is hardly damaged and LC/MS using it can be provided.

Besides, according to the invention, the LC/MS interface that inhibits the extension of the separation band and the deterioration of detection sensitivity and that enables high separation and sensitive analysis and LC/MS using it can be provided.

Further, according to the invention, the LC/MS interface which a general user can use without a sense of incompatibility and the operability of which is high and LC/MS using it can be provided.

What is claimed is:

1. A mass spectrometer, comprising:
a pump for conveying a sample;
a tube for conveying the sample;
a spray tube for taking the sample conveyed from the tube;
a metallic member that supports the tube;
a resin member that supports the spray tube;
a mass spectrograph that analyzes the mass of an ion sprayed from the spray tube; and
an information processing unit that processes the result of analysis by the mass spectrograph, wherein:
the resin member is closely in contact with the peripheral surface of the spray tube except an open face at a sample intake end and at least a part of the resin member is in contact with the metallic member; and
a sample outlet of the tube is located in the vicinity of the sample intake end of the spray tube.

2. A mass spectrometer according to claim 1, wherein:
the resin member has a hole for inserting the spray tube; and
the hole is tapered along the spray tube.

3. A mass spectrometer according to claim 1, wherein:
the resin member and the metallic member are fixed by a fixture.

4. A mass spectrometer according to claim 1, wherein:
the central axis of the tube and the central axis of the spray tube are substantially aligned.

5. A mass spectrometer according to claim 1, wherein:
the central axis of the resin member and the central axis of the metallic member are substantially aligned.

6. A mass spectrometer, comprising:
a pump for conveying a sample;
a tube for conveying the sample;
a spray tube for taking the sample conveyed from the tube;
a metallic member that supports the tube;
a housing that houses the metallic member;
a resin member that supports the spray tube;
a mass spectrograph that analyzes the mass of an ion sprayed from the spray tube; and
an information processing unit that processes the result of analysis by the mass spectrograph, wherein:
a sample outlet of the tube is located in the vicinity of the sample intake end of the spray tube; and
the housing and the resin member are fitted.

7. A mass spectrometer according to claim 6, wherein:
the resin member has concave and convex portions;
the resin member is in contact with at least a part of the housing on the side of either of the concave or convex portions; and
the resin member is in contact with at least a part of the metallic member on the side of the other of the concave and convex portions.

8. A mass spectrometer according to claim 6, further comprising:
a first fixture for fixing the resin member and the metallic member;
a keep member; and
a second fixture for fixing the resin member and the housing.

9. A mass spectrometer, comprising:
a pump for conveying a sample;
a tube for conveying the sample;
a spray tube for taking the sample conveyed from the tube;
a first supporting member that supports the tube;
a second supporting member that supports the spray tube;
a mass spectrograph that analyzes the mass of an ion sprayed from the spray tube; and
an information processing unit that processes the result of analysis by the mass spectrograph, wherein:
the second supporting member is made of material having lower hardness than that of the first supporting member; and
a sample outlet of the tube is located in the vicinity of the sample intake end of the spray tube.

10. A mass spectrometer according to claim 9, wherein:
the tube is a separation column or a capillary.

11. A mass spectrometer according to claim 9, wherein:
the tube is fixed to the metallic member by a fixture.

12. A mass spectrometer according to claim 9, further comprising:
a sleeve that houses at least a part of the tube.

13. A mass spectrometer according to claim 9, wherein:
the tube is in contact with an opening having a smaller inside diameter than the outside diameter of the sample outlet of the tube of the metallic member; and
the sample outlet of the tube and the sample intake end of the spray tube are arranged via the opening of the metallic member.

14. A mass spectrometer according to claim 9, wherein:
the length of the spray tube is in a range from approximately 1 mm to approximately 50 mm;
at least a part of the resin member is in contact with a fitting part provided to the metallic member; and
the sample outlet of the tube and the sample intake end of the spray tube are located close to the inside of the fitting part.

15. A mass spectrometer according to claim 9, wherein:
the length of a part located outside the resin member of the spray tube is in a range from approximately 0.1 mm to approximately 50 mm.

16. A mass spectrometer according to claim 13, wherein:
the length in a direction of the main flow of the sample of the opening is in a range from approximately 0.01 mm to approximately 0.5 mm.

17. A mass spectrometer according to claim 9, further comprising:
a metallic cover which is in contact with at least a part of the resin member and which is located in the vicinity of the sample outlet of the spray tube.

18. A mass spectrometer according to claim 9, further comprising:
gas intake means an open end of which is located in the vicinity of the spray tube.

19. A mass spectrometer according to claim 9, further comprising:
a capillary connected to the pump and the tube; and
a union for connecting the capillary and the tube.

20. A member for mass spectrometry, comprising:
a tube for conveying a sample;
a spray tube for taking the sample conveyed from the tube;
a metallic member that supports the tube;
a resin member that supports the spray tube; and
a cover that covers a part protruded outside the resin member of the spray tube, wherein:
the resin member is closely in contact with the peripheral surface except an open face at a sample intake end of the spray tube and at least a part of the resin member is in contact with the metallic member; and
a sample outlet of the tube is located in the vicinity of the sample intake end of the spray tube.

* * * * *